(12) United States Patent
Achen et al.

(10) Patent No.: US 6,730,489 B1
(45) Date of Patent: May 4, 2004

(54) ANTIBODIES TO TRUNCATED VEGF-D AND USES THEREOF

(75) Inventors: Marc G. Achen, Parkville (AU); Steven Alan Stacker, Parkville (AU)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 10/100,037

(22) Filed: Mar. 19, 2002

Related U.S. Application Data

(62) Division of application No. 09/469,186, filed on Dec. 21, 1999, now Pat. No. 6,383,484.
(60) Provisional application No. 60/134,556, filed on May 17, 1999, and provisional application No. 60/113,254, filed on Dec. 21, 1998.

(51) Int. Cl.[7] .......................... G01N 33/53; C12N 5/12; C07K 16/00; C07K 1/00; C12P 21/08
(52) U.S. Cl. ................. 435/7.1; 530/387.1; 530/387.3; 530/388.23; 530/391.1; 530/391.3; 530/809; 435/326
(58) Field of Search ............... 435/7.1, 326; 530/391.1, 530/391.3, 387.1, 387.3, 388.29, 809

(56) References Cited

FOREIGN PATENT DOCUMENTS

| | | | |
|---|---|---|---|
| WO | WO 98/07832 | * | 2/1998 |
| WO | WO 98/33917 | | 8/1998 |
| WO | WO 99/33485 | | 7/1999 |

OTHER PUBLICATIONS

Kuby et al., 1994, Immunology, second edition, pp. 85–96.*
Abaza et al, J of Protein Chemistry 11(5): 433–444, 1992.*
Harlow et al, in Antibodies a Laboratory Manual, 1988, Cold Spring harbor laboratory publication, Cold Spring Harbor, NY, p. 319–329, and pp. 626–629.*
Joukov et al (EMBO J 16(13): 3898–3911, 1997.*
U.S. patent application Ser. No. 08/915,795, filed Aug. 21, 1997.
U.S. patent application Ser. No. 09/296,275, filed Apr. 22, 1999.
Marc Achen et al. "Vascular Endothelial Growth Factor D (VEGF–D) is a Ligand for the Tyrosine Kinases VEGF Receptor 2 (FLK1) and VEGF Receptor 3 (FLT4)" *Proc. Natl. Acad. Sci. USA*, vol. 95, No. 2, pp. 548–553 (1998). XP–002066364.

* cited by examiner

*Primary Examiner*—Christina Chan
*Assistant Examiner*—Phuong Huynh
(74) *Attorney, Agent, or Firm*—Crowell & Moring LLP

(57) ABSTRACT

The invention is based on the isolation of antibodies that were made to a polypeptide having the amino acid sequence for a truncated VEGF-D. One of these antibodies can interfere with the activity of VEGF-D mediated by VEGFR-2 and interfere with the binding of VEGF-D to VEGFR-3 but does not interfere with the activity of VEGF mediated by VEGFR-2 or bind to VEGF-C. The invention provides pharmaceutical and diagnostic compositions and methods utilizing these antibodies.

20 Claims, 5 Drawing Sheets

Phe Tyr Asp Ile Glu Thr Leu Lys Val Ile Asp Glu Glu Trp Gln Arg
1                 5                  10                 15
Thr Gln Cys Ser Pro Arg Glu Thr Cys Val Glu Val Ala Ser Glu Leu
              20                  25                  30
Gly Lys Ser Thr Asn Thr Phe Phe Lys Pro Pro Cys Val Asn Val Phe
              35                  40                  45
Arg Cys Gly Gly Cys Cys Asn Glu Glu Ser Leu Ile Cys Met Asn Thr
          50                  55                  60
Ser Thr Ser Tyr Ile Ser Lys Gln Leu Phe Glu Ile Ser Val Pro Leu
65                  70                  75                  80
Thr Ser Val Pro Glu Leu Val Pro Val Lys Val Ala Asn His Thr Gly
              85                  90                  95
Cys Lys Cys Leu Pro Thr Ala Pro Arg His Pro Tyr Ser
              100                 105

FIG. 1

ANTIBODIES TO TRUNCATED VEGF-D AND USES THEREOF

CROSS REFERENCE TO RELATED APPLICATIONS

This application claims the benefit of U.S. Provisional Application No. 60/113,254, filed Dec. 21, 1998; and U.S. Provisional Application No. 60/134,556, filed May 17, 1999; and is a divisional application of U.S. patent application Ser. No. 09/469,186, filed Dec. 21, 1999, now U.S. Pat. No. 6,383,484.

FIELD OF THE INVENTION

This invention relates to a composition of matter which comprises an antibody that is specifically reactive with a polypeptide having the amino acid sequence as set forth in FIG. 1 (SEQ ID NO:1). The antibody includes monoclonal antibodies (MAbs), immunoreactive fragments or recombinants thereof. The invention also relates to pharmaceutical and diagnostic compositions and methods utilizing these antibodies.

BACKGROUND OF THE INVENTION

In the developing embryo, the primary vascular network is established by in situ differentiation of mesodermal cells in a process called vasculogenesis. It is believed that all subsequent processes involving the generation of new vessels in the embryo and neovascularization in adults, are governed by the sprouting or splitting of new capillaries from the pre-existing vasculature in a process called angiogenesis (Pepper et al., *Enzyme & Protein*, 49: 138–162, 1996; Breier et al., *Dev. Dyn.*, 204: 228–239, 1995; Risau, *Nature*, 386: 671–674, 1997). Angiogenesis is not only involved in embryonic development and normal tissue growth, repair, and regeneration, but is also involved in the female reproductive cycle, establishment and maintenance of pregnancy, and in repair of wounds and fractures. In addition to angiogenesis which takes place in the normal individual, angiogenic events are involved in a number of pathological processes, notably tumor growth and metastasis, and other conditions in which blood vessel proliferation, especially of the microvascular system, is increased, such as diabetic retinopathy, psoriasis and arthropathies. Inhibition of angiogenesis is useful in preventing or alleviating these pathological processes.

On the other hand, promotion of angiogenesis is desirable in situations where vascularization is to be established or extended, for example after tissue or organ transplantation, or to stimulate establishment of collateral circulation in tissue infarction or arterial stenosis, such as in coronary heart disease and thromboangitis obliterans.

The angiogenic process is highly complex and involves the maintenance of the endothelial cells in the cell cycle, degradation of the extracellular matrix, migration and invasion of the surrounding tissue and finally, tube formation. The molecular mechanisms underlying the complex angiogenic processes are far from being understood.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor alpha (TGFα), and hepatocyte growth factor (HGF). See for example Folkman et al., *J. Biol. Chem.*, 267:–10931–10934, 1992 for a review.

It has been suggested that a particular family of endothelial cell-specific growth factors, the vascular endothelial growth factors (VEGFs), and their corresponding receptors is primarily responsible for stimulation of endothelial cell growth and differentiation, and for certain functions of the differentiated cells. These factors are members of the PDGF family, and appear to act primarily via endothelial receptor tyrosine kinases (RTKs).

Nine different proteins have been identified in the PDGF family, namely two PDGFs (A and B), VEGF and six members that are closely related to VEGF. The six members closely related to VEGF are: VEGF-B, described in International Patent Application PCT/US96/02957 (WO 96/26736) and in U.S. Pat. Nos. 5,840,693 and 5,607,918 by Ludwig Institute for Cancer Research and The University of Helsinki; VEGF-C, described in Joukov et al., *EMBO J.*, 15: 290–298, 1996 and Lee et al., *Proc. Natl. Acad. Sci. USA*, 93: 1988–1992, 1996; VEGF-D, described in International Patent Application No. PCT/US97/14696 (WO 98/07832), and Achen et al., *Proc. Natl. Acad. Sci. USA*, 95: 548–553, 1998; the placenta growth factor (PlGF), described in Maglione et al., *Proc. Natl. Acad. Sci. USA*, 88: 9267–9271, 1991; VEGF2, described in International Patent Application No. PCT/US94/05291 (WO 95/24473) by Human Genome Sciences, Inc; and VEGF3, described in International Patent Application No. PCT/US95/07283 (WO 96/39421) by Human Genome Sciences, Inc. Each VEGF family member has between 30% and 45% amino acid sequence identity with VEGF. The VEGF family members share a VEGF homology domain which contains the six cysteine residues which form the cysteine knot motif. Functional characteristics of the VEGF family include varying degrees of mitogenicity for endothelial cells, induction of vascular permeability and angiogenic and lymphangiogenic properties.

Vascular endothelial growth factor (VEGF) is a homodimeric glycoprotein that has been isolated from several sources. VEGF shows highly specific mitogenic activity for endothelial cells. VEGF has important regulatory functions in the formation of new blood vessels during embryonic vasculogenesis and in angiogenesis during adult life (Carmeliet et al., *Nature*, 380: 435–439, 1996; Ferrara et al., *Nature*, 380: 439–442, 1996; reviewed in Ferrara and Davis-Smyth, *Endocrine Rev.*, 18: 4–25, 1997). The significance of the role played by VEGF has been demonstrated in studies showing that inactivation of a single VEGF allele results in embryonic lethality due to failed development of the vasculature (Carmeliet et al., *Nature*, 380: 435–439, 1996; Ferrara et al., *Nature*, 380: 439–442, 1996). In addition VEGF has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). The isolation and properties of VEGF have been reviewed; see Ferrara et al., *J. Cellular Biochem.*, 47: 211–218, 1991 and Connolly, *J. Cellular Biochem.*, 47: 219–223, 1991. Alterative mRNA splicing of a single VEGF gene gives rise to five isoforms of VEGF.

VEGF-B has similar angiogenic and other properties to those of VEGF, but is distributed and expressed in tissues differently from VEGF. In particular, VEGF-B is very strongly expressed in heart, and only weakly in lung, whereas the reverse is the case for VEGF. This suggests that VEGF and VEGF-B, despite the fact that they are co-expressed in many tissues, may have functional differences.

VEGF-B was isolated using a yeast co-hybrid interaction trap screening technique by screening for cellular proteins which might interact with cellular resinoid acid-binding protein type I (CRABP-I). Its isolation and characteristics are described in detail in PCT/US96/02957 and in Olofsson et al., *Proc. Natl. Acad. Sci. USA*, 93: 2576–2581, 1996.

VEGF-C was isolated from conditioned media of the PC-3 prostate adenocarcinoma cell line (CRL1435) by screening for ability of .e medium to produce tyrosine phosphorylation of the endothelial cell-specific receptor tyrosine kinase VEGFR-3 (Flt4), using cells transfected to express VEGFR-3. VEGF-C was purified using affinity chromatography with recombinant VEGFR-3, and was cloned from a PC-3 cDNA library. Its isolation and characteristics are described in detail in Joukov et al., *EMBO J.*, 15: 290–298, 1996.

VEGF-D was isolated from a human breast cDNA library, commercially available from Clontech, by screening with an expressed sequence tag obtained from a human cDNA library designated "Soares Breast 3NbHBst" as a hybridization probe (Achen et al., *Proc. Natl. Acad. Sci. USA*, 95: 548–553, 1998). Its isolation and characteristics are described in detail in International Patent Application No. PCT/US97/14696 (WO98/07832).

The VEGF-D gene is broadly expressed in the adult human, but is certainly not ubiquitously expressed. VEGF-D is strongly expressed in heart, lung and skeletal muscle. Intermediate levels of VEGF-D are expressed in spleen, ovary, small intestine and colon, and a lower expression occurs in kidney, pancreas, thymus, prostate and testis. No VEGF-D mRNA was detected in RNA from brain, placenta, liver or peripheral blood leukocytes.

PlGF was isolated from a term placenta cDNA library. Its isolation and characteristics are described in detail in Maglione et al., *Proc. Natl. Acad. Sci. USA*, 88: 9267–9271, 1991. Presently its biological function is not well understood.

VEGF2 was isolated from a highly tumorgenic, oestrogen-independent human breast cancer cell line. While this molecule is stated to have about 22% homology to PDGF and 30% homology to VEGF, the method of isolation of the gene encoding VEGF2 is unclear, and no characterization of the biological activity is disclosed.

VEGF3 was isolated from a cDNA library derived from colon tissue. VEGF3 is stated to have about 36% identity and 66% similarity to VEGF. The method of isolation of the gene encoding VEGF3 is unclear and no characterization of the biological activity is disclosed.

Similarity between two proteins is determined by comparing the amino acid sequence and conserved amino acid substitutions of one of the proteins to the sequence of the second protein, whereas identity is determined without including the conserved amino acid substitutions.

PDGF/VEGF family members act primarily by binding to receptor tyrosine kinases. Five endothelial cell-specific receptor tyrosine kinases have been identified, namely VEGFR-1 (Flt-1), VEGFR-2 (KDR/Flk-1), VEGFR-3 (Flt4), Tie and Tek/Tie-2. All of these have the intrinsic tyrosine kinase activity which is necessary for signal transduction. The essential, specific role in vasculogenesis and angiogenesis of VEGFR-1, VEGFR-2, VEGFR-3, Tie and Tek/Tie-2 has been demonstrated by targeted mutations inactivating these receptors in mouse embryos.

The only receptor tyrosine kinases known to bind VEGFs are VEGFR-1, VEGFR-2 and VEGFR-3. VEGFR-1 and VEGFR-2 bind VEGF with high affinity, and VEGFR-1 also binds VEGF-B and PlGF. VEGF-C has been shown to be the ligand for VEGFR-3, and it also activates VEGFR-2 (Joukov et al., The *EMBO Journal*, 15: 290–298, 1996).

VEGF-D binds to both VEGFR-2 and VEGFR-3. A ligand for Tek/Tie-2 has been described in International Patent Application No. PCT/US95/12935 (WO 96/11269) by Regeneron Pharmaceuticals, Inc. The ligand for Tie has not yet been identified.

Recently, a novel 130–135 kDa VEGF isoform specific receptor has been purified and cloned (Soker et al., *Cell*, 92: 735–745, 1998). The VEGF receptor was found to specifically bind the $VEGF_{165}$ isoform via the exon 7 encoded sequence, which shows weak affinity for heparin (Soker et al., *Cell*, 92: 735–745, 1998). Surprisingly, the receptor was shown to be identical to human neuropilin-1 (NP-1), a receptor involved in early stage neuromorphogenesis. PlGF-2 also appears to interact with NP-1 (Migdal et al., *J. Biol. Chem.*, 273: 22272–22278, 1998).

VEGFR-1, VEGFR-2 and VEGFR-3 are expressed differently by endothelial cells. Both VEGFR-1 and VEGFR-2 are expressed in blood vessel endothelia (Oelrichs et al., *Oncogene*, 8: 11–18, 1992; Kaipainen et al., *J. Exp. Med.*, 178: 2077–2088, 1993; Dumont et al., *Dev. Dyn.*, 203: 80–92, 1995; Fong et al., *Dev. Dyn.*, 207: 1–10, 1996) and VEGFR-3 is mostly expressed in the lymphatic endothelium of adult tissues (Kaipainen et al., *Proc. Natl. Acad. Sci. USA*, 9: 3566–3570, 1995). VEGFR-3 is also expressed in the blood vasculature surrounding tumors.

Disruption of the VEGFR genes results in aberrant development of the vasculature leading to embryonic lethality around midgestation. Analysis of embryos carrying a completely inactivated VEGFR-1 gene suggests that this receptor is required for functional organization of the endothelium (Fong et al., *Nature*, 376: 66–70, 1995). However, deletion of the intracellular tyrosine kinase domain of VEGFR-1 generates viable mice with a normal vasculature (Hiratsuka et al., *Proc. Natl. Acad. Sci. USA*, 95: 9349–9354, 1998). The reasons underlying these differences remain to be explained but suggest that receptor signalling via the tyrosine kinase is not required for the proper function of VEGFR-1. Analysis of homozygous mice with inactivated alleles of VEGFR-2 suggests that this receptor is required for endothelial cell proliferation, hematopoesis and vasculogenesis (Shalaby et al., *Nature*, 376: 62–66, 1995; Shalaby et al., *Cell*, 89: 981–990, 1997). Inactivation of VEGFR-3 results in cardiovascular failure due to abnormal organization of the large vessels (Dumont et al. *Science*, 282: 946–949, 1998).

Although VEGFR-1 is mainly expressed in endothelial cells during development, it can also be found in hematopoetic precursor cells during early stages of embryogenesis (Fong et al., *Nature*, 376: 66–70, 1995). In adults, monocytes and macrophages also express this receptor (Barleon et al., *Blood*, 87: 3336–3343, 1995). In embryos, VEGFR-1 is expressed by most, if not all, vessels (Breier et al., *Dev. Dyn.*, 204: 228–239, 1995; song et al., *Dev. Dyn.*, 207: 1–10, 1996).

The receptor VEGFR-3 is widely expressed on endothelial cells during early embryonic development but as embryogenesis proceeds becomes restricted to venous endothelium and then to the lymphatic endothelium (Kaipainen et al., *Cancer Res.*, 54: 6571–6577, 1994; Kaipainen et al., *Proc. Natl. Acad. Sci. USA*, 92: 3566–3570, 1995). VEGFR-3 is expressed on lymphatic endothelial cells in adult tissues. This receptor is essential for vascular development during embryogenesis. Targeted inactivation of both copies of the VEGFR-3 gene in mice resulted in defective blood vessel formation characterized by abnormally organized large vessels with defective lumens, leading to fluid accumulation in the pericardial cavity and cardiovascular failure at post-coital day 9.5. On the basis of these findings it has been proposed that VEGFR-3 is required for the maturation of primary vascular networks into larger blood vessels. However, the role of VEGFR-3 in the development of the lymphatic vasculature could not be studied in these mice because the embryos died before the lymphatic system emerged. Nevertheless it is assumed that VEGFR-3 plays a role in development of the lymphatic vasculature and lymphangiogenesis given its specific expression in lymphatic endothelial cells during embryogenesis and adult life. This is supported by the finding that ectopic expression of VEGF-C, a ligand for VEGFR-3, in the skin of transgenic mice, resulted in lymphatic endothelial cell proliferation and vessel enlargement in the dermis. Furthermore this suggests that VEGF-C may have a primary function in lymphatic endothelium, and a secondary function in angiogenesis and permeability regulation which is shared with VEGF (Joukov et al., *EMBO J.*, 15: 290–298, 1996)

Some inhibitors of the VEGF/VEGF-receptor system have been shown to prevent tumor growth via an anti-angiogenic mechanism; see Kim et al., *Nature*, 362: 841–844, 1993 and Saleh et al., *Cancer Res.*, 56: 393–401, 1996.

SUMMARY OF THE INVENTION

The invention generally provides a composition of matter which comprises an antibody specifically reactive with a polypeptide having the amino acid sequence as set forth in FIG. 1 (SEQ ID NO:1), where the antibody is a monoclonal antibody (MAb), an immunoreactive fragment or a recombinant thereof. In another embodiment of the invention, the composition of matter comprises an antibody that can interfere with the activity of VEGF-D mediated by the mammalian VEGFR-2 and/or interfere with the binding of VEGF-D to the mammalian VEGFR-3. A particularly preferred antibody can interfere with the activity of VEGF-D mediated by VEGFR-2 and/or interfere with the binding of VEGF-D to VEGFR-3 but not with the activity of VEGF mediated by VEGFR-2 and/or bind to VEGF-C. The invention also relates to pharmaceutical and diagnostic compositions and methods utilizing the antibody.

According to a first aspect, the invention provides for a composition of matter which comprises an antibody specifically reactive with the polypeptide having the amino acid sequence as set forth in FIG. 1 (SEQ ID NO:1) Examples of such antibodies include the monoclonal antibodies (MAbs) designated 2F8, 4A5, 4E10, 5F12, 4H4 and 3C10.

According to a second aspect, the invention provides a composition of matter which comprises an antibody which interferes with the activity of VEGF-D mediated by the VEGFR-2. In a preferred embodiment this antibody also interferes with the binding of VEGF-D to VEGFR-3 but does not interfere with the activity of VEGF mediated by the VEGFR-2 and/or bind to VEGF-C. An example of such an antibody is the antibody MAb 4A5 which has the isotype, $IgG_1$.

In a third aspect, the invention provides a composition of matter which comprises an antibody which interferes with the binding of VEGF-D to VEGFR-3.

Antibodies can be raised against the polypeptide having the amino acid sequence as set forth in FIG. 1 (SEQ ID NO:1) or a fragment of the polypeptide using standard methods in the art. In addition this polypeptide can be linked to an epitope tag, such as the FLAG® octapeptide (Sigma, St. Louis, Mo.), to assist in affinity purification. For some purposes, for example where an antibody is to be used to inhibit effects of VEGF-D in a clinical situation, it may be desirable to use humanized or chimeric monoclonal antibodies or immunoreactive fragments thereof. Methods for producing these are given below, and are also well known in the art, including recombinant DNA methods.

These aspects of the invention also include MAbs, immunoreactive fragments or recombinants thereof, and they may all be suitably labeled.

Antibodies according to the invention may be labeled with a detectable label and utilized for diagnostic purposes. The antibody may be covalently or non-covalently coupled to a suitable supermagnetic, paramagnetic, electron dense, ecogenic or radioactive agent for imaging. For use in diagnostic assays, radioactive or non-radioactive labels may be used. Examples of radioactive labels include a radioactive atom or group, such as $^{125}I$ or $^{32}P$. Examples of non-radioactive labels include enzymatic labels, such as horseradish peroxidase, or fluorimetric labels, such as fluorescein-5-isothiocyanate (FITC). Labeling may be direct or indirect, covalent or non-covalent.

A fourth aspect of the invention relates to a method for preparing a monoclonal antibody that is specifically reactive with a polypeptide having the amino acid sequence as set forth in FIG. 1 (SEQ ID NO:1). In addition this polypeptide can be linked to an epitope tag, such as the FLAG® octapeptide(Sigma-Aldrich) The method comprises the steps of immunizing an immunocompetent mammal with an immunogen comprising a polypeptide having the amino acid sequence as set forth in FIG. 1 (SEQ ID NO:1) or a fragment of the polypeptide and, optionally, a linked epitope tag; fusing lymphocytes of the immunized immunocompetent mammal with myeloma cells to form hybridoma cells; screening monoclonal (MAbs) produced by the hybridoma cells for specific binding activity to the polypeptide having the amino acid sequence as set forth in FIG. 1 (SEQ ID NO:1; culturing a hybridoma cell producing MAbs having specific binding activity to the polypeptide having the amino acid sequence as set forth in FIG. 1 (SEQ ID NO:1) in a medium to proliferate and/or to secrete said monoclonal antibody; and recovering said monoclonal antibody from the culture supernatant.

In addition, a method is provided for preparing a monoclonal antibody that interferes with the activity of VEGF-D mediated by VEGFR-2 and/or interferes with the binding of VEGF-D with VEGFR-3. This method comprises the steps of immunizing an immunocompetent mammal with an immunogen comprising a polypeptide having the amino acid sequence as set forth in FIG. 1 (SEQ ID NO:1) or a fragment of the polypeptide and, optionally, a linked epitope tag; fusing lymphocytes of the immunized immunocompetent mammal with myeloma cells to form hybridoma cells; screening MAbs produced by the hybridoma cells for VEGF-D interfering activity and/or VEGF-D binding interfering activity; culturing a hybridoma cell producing MAbs having VEGF-D interfering activity and/or VEGF-D binding interfering activity in a medium to proliferate and/or to secrete said monoclonal antibody; and recovering said monoclonal antibody from the culture supernatant. In both methods the preferred immunocompetent mammal is a mouse or a rat.

A fifth aspect of the invention is a hybridoma cell that produces a monoclonal antibody that is specifically reactive with a polypeptide having the amino acid sequence as set forth in FIG. 1 (SEQ ID NO:1) or that interferes with the activity of VEGF-D mediated by the VEGFR-2 and/or interferes with VEGF-D binding to VEGFR-3.

A sixth aspect of the invention provides a method for preparing a hybridoma that produces a monoclonal antibody that is specifically reactive with a polypeptide having the amino acid sequence as set forth in FIG. 1 (SEQ ID NO:1) and/or that interferes with the activity of VEGF-D mediated by the VEGFR-2 and/or interferes with VEGF-D binding to VEGFR-3 which comprises the steps of immunizing an immunocompetent mammal with an immunogen comprising a polypeptide having the amino acid sequence as set forth in FIG. 1 (SEQ ID NO:1) or a fragment of the polypeptide and, optionally, a linked epitope tag; obtaining lymphocytes of the immunized immunocompetent mammal; fusing the lymphocytes with myeloma cells to form hybridoma cells; screening MAbs produced by the hybridoma cells for specific binding activity to the polypeptide having the amino acid sequence as set forth in FIG. 1 (SEQ ID NO:1) and/or VEGF-D interfering activity and/or VEGF-D binding interfering activity; and culturing a hybridoma cell that produces said monoclonal antibody having specific binding activity to the polypeptide having the amino acid sequence as set forth in FIG. 1 (SEQ ID NO:1) and/or VEGF-D interfering activity and/or VEGF-D binding interfering activity.

The term "culturing" refers to the cloning of the hybridoma cell by causing it to proliferate and to the induction of the hybridoma to secrete the antibodies described above.

A further aspect of the invention provides a method of interfering with at least one biological activity induced by VEGF-D in a mammal or in a cell culture which comprises the step of administering to said mammal or adding to said cell culture an effective biological activity interfering amount of the monoclonal antibody.

The "biological activities induced by VEGF-D" can be readily tested by methods known in the art. In particular, VEGF-D has the ability to stimulate endothelial cell proliferation or differentiation, including, but not limited to, proliferation or differentiation of vascular endothelial cells and/or lymphatic endothelial cells. Other biological activities contemplated include angiogenesis, lymphangiogenesis and induction of permeability of blood vessels and lymphatic vessels.

The term "antibodies" or "antibody" refers to the composition of matter which comprises an antibody that can interfere with the activity of VEGF-D mediated by the mammalian VEGFR-2 and/or interfere with the binding of VEGF-D to the mammalian VEGFR-3. A particularly preferred antibody can interfere with the activity of VEGF-D mediated by VEGFR-2 and/or interfere with the binding of VEGF-D to VEGFR-3 but not with the activity of VEGF mediated by VEGFR-2 and/or bind to VEGF-C.

Another aspect of the invention concerns the provision of a pharmaceutical composition comprising a therapeutically effective amount of an antibody, and a pharmaceutically acceptable non-toxic salt thereof, and a pharmaceutically acceptable solid or liquid carrier or adjuvant. Examples of such a carrier or adjuvant include, but are not limited to, saline, buffered saline, Ringer's solution, mineral oil, talc, corn starch, gelatin, lactose, sucrose, microcrystalline cellulose, kaolin, mannitol, dicalcium phosphate, sodium chloride, alginic acid, dextrose, water, glycerol, ethanol, thickeners, stabilizers, suspending agents and combinations thereof. Such compositions may be in the form of solutions, suspensions, tablets, capsules, creams, salves, elixirs, syrups, wafers, ointments or other conventional forms. The formulation to suit the mode of administration. Compositions comprising PDGF-C will contain from about 0.1% to 90% by weight of the active compound(s), and most generally from about 10% to 30%.

The dose(s) and route of administration will depend upon the nature of the patient and condition to be treated, and will be at the discretion of the attending physician or veterinarian. Suitable routes include oral, subcutaneous, intramuscular, intraperitoneal or intravenous injection, parenteral, topical application, implants etc. For example, an effective amount of an antibody is administered to an organism in need thereof in a dose between about 0.1 and 1000 µg/kg body weight.

Clinical applications of the invention include diagnostic applications and suppression or inhibition of angiogenesis and/or lymphangiogenesis in the treatment of cancer, diabetic retinopathy, psoriasis and arthopathies. Thus the invention also relates to a method of interfering with angiogenesis, lymphagiogenesis and/or neovascularization in a mammal in need of such treatment which comprises the step of administering an effective amount of an antibody to the mammal. The antibody interferes with the action of VEGF-D by preventing the activation of at least VEGFR-2.

In addition, this aspect of the invention provides a method of interfering with at least one biological activity selected from angiogenesis, lymphangiogenesis and neovascularization in a disease in a mammal selected from the group of cancer, diabetic retinopathy, psoriasis and arthopathies, comprising the step of administering to said mammal an effective angiogenesis, lymphangiogenesis or neovascularization interfering amount of the antibody. As noted above, the antibody interferes with the action of VEGF-D at least in part by interfering with the activity of VEGF-D mediated by VEGFR-2 and/or with the binding of VEGF-D to VEGFR-3.

The antibodies can be used to treat conditions, such as congestive heart failure, involving accumulations of fluid in, for example, the lung resulting from increases in vascular permeability, by exerting an offsetting effect on vascular permeability in order to counteract the fluid accumulation. Accordingly, the invention provides a method for treating fluid accumulation in the heart and/or lung due to increases in vascular permeability in a mammal. This method comprises administering to said mammal in need of such treatment an effective vascular permeability decreasing amount of an antibody.

The invention also provides a method of detecting VEGF-D in a biological sample, comprising the step of contacting the sample with an antibody, and detecting binding involving the antibody. In a preferred embodiment the binding and/or extent of binding is detected by means of a detectable label; suitable labels are discussed above.

According to yet a further aspect, the invention provides a diagnostic/prognostic device typically in the form of a test kit. For example, in one embodiment of the invention there is provided a diagnostic/prognostic test kit comprising the antibody to the polypeptide of FIG. 1 (SEQ ID NO: 1) and means for detecting the binding between the antibody and VEGF-D. In one preferred embodiment of the diagnostic/prognostic device according to the invention, a second antibody (a secondary antibody) directed against antibodies of the same isotype and animal source of the antibody directed against polypeptide of FIG. 1 (SEQ ID NO:1) (the primary antibody) is provided. The secondary antibody is coupled to a detectable label and then either an unlabeled primary antibody or VEGF-D is substrate-bound so that the VEGF-D/primary antibody interaction can be established by determining the amount of label bound to the substrate following binding between the primary antibody and VEGF-D and the subsequent binding of the labeled secondary antibody to the primary antibody. In a particularly preferred embodiment of the invention, the diagnostic/prognostic device may be provided as a conventional enzyme-linked immunosorbent assay (ELISA) kit.

According to yet a further aspect, the invention provides a method for identifying a compound which interferes with the interaction between VEGFR-3 and VEGF-D. This method comprises applying a polypeptide having the extracellular domain of VEGFR-3 to a substrate, incubating the substrate with VEGF-D in the presence of the compound to be identified, and detecting any interaction between VEGFR-3 and VEGF-D.

According to yet a further aspect, the invention provides a method for imaging of lymphatic vasculature in tissue, which comprises contacting the tissue with an antibody, and detecting the occurrence of binding of the antibody.

BRIEF DESCRIPTION OF THE DRAWINGS

FIG. 1 shows the amino acid sequence of the polypeptide (without the FLAG® octapeptide) used to raise the antibodies (SEQ ID NO:1).

DETAILED DESCRIPTION OF PREFERRED EMBODIMENTS

Figure 2:
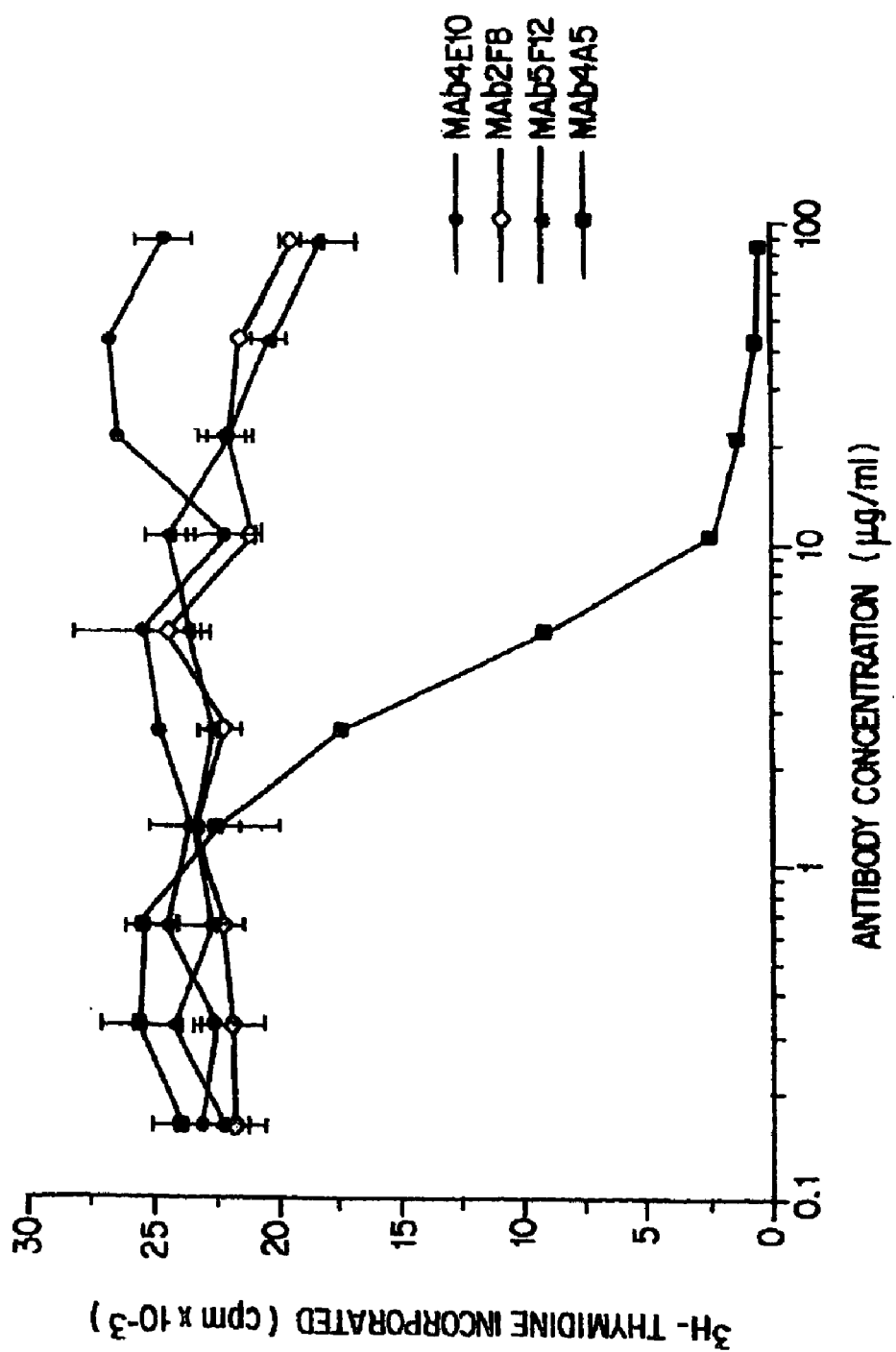
FIG. 2 shows the effects of the monoclonal antibodies on the response of Ba/F3-NYK-EpoR cells to VEGF-DΔNΔC.

FIG. 1 shows the amino acid sequence of the polypeptide without the FLAG® octapeptide (SEQ ID NO:1) used to raise the antibodies.

EXAMPLE I

Antibody Production

Monoclonal antibodies to the polypeptide having the amino acid sequence set forth in FIG. 1 (SEQ ID NO:1) were raised in mice. The polypeptide used as the immunogen to raise the antibodies of the present invention was FLAG®-tagged at its N-terminus (see the description below). This amino acid sequence is the central region of VEGF-D and is similar in sequence to all other members of the VEGF family. Therefore, it is thought that the bioactive portion of VEGF-D likely resides in the conserved region. A DNA fragment encoding a truncated portion of human VEGF-D from residue 93 to 201, i.e. with the N- and C-terminal regions removed, was amplified by polymerase chain reaction (PCR) with Pfu DNA polymerase, using as template a plasmid comprising full-length human VEGF-D cDNA. The amplified DNA fragment, the sequence of which was confirmed by nucleotide sequencing, was then inserted into the expression vector pEFBOSSFLAG (a gift from Dr. Clare McFarlane at the Walter and Eliza Hall Institute for Medical Research (WEHI), Melbourne, Australia) to give rise to a plasmid designated pEFBOSVEGF-DΔNΔC. The pEFBOSSFLAG vector contains DNA encoding the signal sequence for protein secretion from the interleukin-3 (IL-3) gene and the FLAG® octapeptide. The FLAG® octapeptide (Sigma, St. Louis, Mo.) can be recognized by commercially available antibodies such as the M2 monoclonal antibody (Sigma, St. Louis, Mo.). The VEGF-D PCR fragment was inserted into the vector such that the IL-3 signal sequence was immediately upstream from the FLAG® octapeptide, which was in turn immediately upstream from the truncated VEGF-D sequence. All three sequences were in the same reading frame, so that translation of mRNA resulting from transfection of pEFBOSVEGF-DΔNΔC into mammalian cells would give rise to a protein which would have the IL-3 signal sequence at its N-terminus, followed by the FLAG® octapeptide and the truncated VEGF-D sequence. Cleavage of the signal sequence and subsequent secretion of the protein from the cell would give rise to a VGF-D polypeptide which is tagged with the FLAG® octapeptide adjacent to the N-terminus. This protein was designated VEGF-DΔNΔC. VEGF-DΔNΔC was purified by anti-FLAG® affinity chromatography from the medium of COS cells which had been transiently transfected with the plasmid pEFBOSVEGF-DΔNΔC. (see Example 9 in International Patent Application No. PCT/US97/14696).

Purified VEGF-DΔNΔC was used to immunize female Balb/C mice on day 85 (intraperitoneal), 71 (intraperitoneal) and 4 (intravenous) prior to the harvesting of the spleen cells from the immunized mice and subsequent fusion of these spleen cells to mouse myeloma P3X63Ag8.653 (NS-1) cells. For the first two immunizations, approximately 10 μg of VEGF-DΔNΔC in a 1:1 mixture of phosphate buffered saline (PBS) and TiterMax adjuvant (#R-1 Research adjuvant; CytRx Corp., Norcross, Ga.) were injected, whereas for the third immunization 35 μg of VEGF-DΔNΔC in PBS was used.

Monoclonal antibodies (MAbs) to VEGF-DΔNΔC were selected by screening the MAbs produced by hybridomas on purified VEGF-DΔNΔC using an enzyme immunoassay. Briefly, 96-well microtiter plates were coated with VEGF-DΔNΔC and hybridoma supernatants were added and incubated for 2 hours at 4° C., followed by six washes in PBS with 0.02% Tween 20. Incubation with a horse radish peroxidase conjugated anti-mouse Ig (Bio-Rad, Hercules, Calif.) followed for 1 hour at 4° C. After washing, the assay was developed with an 2,2'-azino-di-(3-ethylbenz-thiazoline sulfonic acid (ABTS) substrate system (Zymed, San Francisco, Calif.), and the assay was quantified by reading absorbance at 405 nm in a multiwell plate reader (Flow Laboratories MCC/340, McLean, Va.). Six antibodies were selected for further analysis and were subcloned twice by limiting dilution. These antibodies were designated 2F8, 3C10, 4A5, 4E10, 4H4 and 5F12. The isotypes of the antibodies were determined using an Isostrip™ isotyping kit (Boehringer Mannheim, Indianapolis, Ind.). Antibodies 2F8, 4A5, 4E10 and 5F12 were of the IgG$_1$ class whereas 4H4 and 3C10 were of the IgM class. All six antibodies contained the kappa light chain.

EXAMPLE II

Purification of Antibodies

Hybridoma cell lines were grown in Dulbecco's Modified Eagle Medium (DMEM) containing 5% v/v IgG-depleted serum (Gibco BRL, Gaithersburg, Md.), 5 mM L-glutamine, 50 μg/ml gentamicin and 10 μg/ml recombinant IL-6. Antibodies 2F8, 4A5, 4E10 and 5F12 were purified by affinity chromatography using protein G-Sepharose according to the technique of Darby et al., J. Immunol. Methods 159: 125–129, 1993, and the yield assessed by measuring absorption at 280 nm.

The mouse hybridoma cells that produce antibody 5F12 were deposited in the American Type Culture Collection, 10801 University Boulevard, Manassas, Va. 20110-2209 USA on Aug. 20, 2001 (ATCC No. PTA-36511. The mouse hybridoma cells that produce antibody 4E10 were deposited in the American Type Culture Collection, 10801 University Boulevard, Manassas, Va. 20110-2209 USA on Aug. 20, 2001 (ATCC No. PTA-3652). The mouse hybridoma cells that produce antibody 2F8 were deposited in the American Type Culture Collection, 10801 University Boulevard, Manassas, Va. 20110-2209 USA on Aug. 20, 2001 (ATCC No. PTA-3653). The mouse hybridoma cells that produce antibody 4A5 were deposited in the American Type Culture Collection, 10801 University Boulevard, Manassas, Va. 20110-2209 USA on Apr. 16, 1999 (ATCC No. HB-12698). These deposits were made under the requirements of the Budapest Treaty on the International Recognition of the Deposit of Microorganisms for the Purposes of Patent Procedure.

EXAMPLE III

Binding Affinities of the Antibodies for VEGF-D$\Delta$N$\Delta$C

The relative binding affinities of the four anti-VEGF-D$\Delta$N$\Delta$C MAbs, 2F8, 4A5, 4E10 and 5F12, for human VEGF-D$\Delta$N$\Delta$C were determined by analysis of the binding kinetics for these interactions by biosensor studies using surface plasmon resonance according to the techniques of Nice and Catimel, *Bioassays* 21: 339–352, 1999. VEGFR-2-FLAG, VEGFR-3-Ig and anti-VEGF-D monoclonal antibodies were coupled to the carboxymethylated dextran layer of a sensor chip using standard amine coupling chemistry as described in Nice and Catimel, *Bioassays* 21: 339–352, 1999. (VD1 4739 RU, VD2 5268 RU, VD3 5781 RU and VD4 5634 RU immobilized corresponding to 4.7, 5.2, 5.7 and 5.6 ng/mm$^2$ respectively (Stenberg et al., *J. Colloid Interface* 43: 513–526, 1990)). Ligand binding was analyzed using a BIAcore 3000 optical biosensor (BIAcore, Uppsala, Sweden). Automatic targeting of immobilization levels was achieved using BIAcore 3.1 control software (Catimel et al., *J. Chromatogr. A.* 776: 15–30, 1997). Following immobilization, residual activated ester groups were blocked by treatment with 1M ethanolamine hydrochloride pH 8.5. This was followed by washing with 10 mM diethylamine to remove non-convalently bound material as well as to regenerate the sensor surface between analyses. Samples for the assay were diluted in running buffer (10 mM HEPES, pH 7.4, 150 mM NaCl, 3.4 mM EDTA, 0.005% Tween 20). Binding curves were obtained by flowing human VEGF-D$\Delta$N$\Delta$C over the surface (41–689 nM) at a flow rate of 10 $\mu$l/min. For determination of the relative binding affinities of the antibodies for human VEGF-D$\Delta$N$\Delta$C, data were analyzed using BIAevaluation 3.0 (BIAcore, Uppsala, Sweden) as described in Catimel et al.,*J. Chromatogr. A.* 776: 15–30, 1997. The binding constants were obtained by analysis of the initial disassociation phase to obtain the $k_d$, which was then used to constrain a global analysis of the association region of the curves where a 1:1 Langmuirian model was operative. The analyses of the relative binding affinities of the antibodies for human VEGF-D$\Delta$N$\Delta$C are given in the Table below. Since the antibodies were immobilized, a valency of 1 was assumed for the ligand. All antibodies displayed similar affinity ($K_D$'s of 30 to 60 nM) with $k_s$' of between 7.4 and 10.7×10$^4$ M$^{-1}$ s$^{-1}$ and $k_d$'s between 2.1 and 5.2×10$^{-3}$ s$^{-1}$.

| Antibody | $k_s$ (1/Ms) | $k_d$ (1/s) | $K_D$ (M) |
|---|---|---|---|
| 5F12 | 8.6e4 | 5.2e-3 | 6.05e-8 |
| 4A5 | 7.4e4 | 2.16e-3 | 2.98e-8 |
| 4E10 | 7.8e4 | 4.45e-3 | 5.71e-8 |
| 2F8 | 1.07e5 | 3.9e-3 | 3.64e-8 |

EXAMPLE IV

Antibodies which Interfere With the Activity of VEGF-D Mediated by VEGFR-2

The purified monoclonal antibodies (MAbs) 2F8 (ATCC No. PTA-3653), 4A5 (ATCC No. HB-12698), 4E10 (ATCC No. PTA-3652) and 5F12 (ATCC No. PTA-3651) were tested for the ability to interfere with the activity of VEGF-D$\Delta$N$\Delta$C mediated by mouse VEGFR-2 (also known as Flk1 and NyK) using the bioassay described in Example 7 of International patent application No. PCT/US95/14696. The bioassay is also described in International patent application No. PCT/US95/16755. This assay involves the use of Ba/F3 pre-B cells which have been transfected with a plasmid construct encoding a chimeric receptor consisting of the extracellular domain of VEGFR-2 and the cytoplasmic domain of erythropoietin receptor (EpoR) (Ba/F3-NYK-EpoR cells). These cells are routinely passaged in interleukin-3 (IL-3) and will die in the absence of IL-3. However, if signaling is induced from the cytoplasmic domain of the chimeric receptor, these cells survive and proliferate in the absence of IL-3. Such signaling is induced by ligands which bind to the VEGFR-2 extracellular domain of the chimeric receptor. Therefore binding of VEGF-D$\Delta$N$\Delta$C or VEGF to the VEGFR-2 extracellular domain causes the cells to survive and proliferate in the absence of IL3. Addition of antibodies which interfere with the binding of such ligands to the extracellular domain or with the activation of the cytoplasmic domain will cause cell death in the absence of IL-3. Parental Ba/F3 cells which lack the chimeric receptor are not induced by VEGF-D$\Delta$N$\Delta$C or VEGF to proliferate in the absence of IL-3, indicating that the responses of the Ba/F3-NYK-EpoR cells to these ligands is totally dependent on the chimeric receptor.

Samples of purified VEGF-D$\Delta$N$\Delta$C were incubated with varying amounts of antibodies for one hour at 4° C. in PBS before dilution of the mixtures 1:10 with IL-3-deficient cell culture medium. The resulting media contained approximately 500 ng/ml of VEGF-D$\Delta$N$\Delta$C and a range of concentrations of the antibodies up to 100 $\mu$g/ml. Ba/F3-NYK-EpoR cells were then incubated in the media for 48 hours at 37° C. DNA synthesis was then quantified by the addition of 1 $\mu$Ci of $^3$H-thymidine and further incubation for 4 hours prior to harvesting. Incorporated $^3$H-thymidine was measured using a cell harvester (Tomtec®, Orange, Conn.) and beta counting. The effect of antibodies 2F8, 4A5, 4E10 and SF12 on the proliferative response of Ba/F3-NYK-EpoR cells to VEGF-D$\Delta$N$\Delta$C is shown in FIG. 2, in which the data points represent the mean of two experiments and error bars denote the range of the two experiments at each point.

Antibody 4A5 blocked the response of Ba/F3-NYK-EpoR cells to VEGF-D$\Delta$N$\Delta$C in a dose-dependent fashion (FIG. 2). Inclusion of antibody 4A5 at 40 $\mu$g/mi in the cell culture medium was sufficient to totally block the response of the cells. In contrast, the other three antibodies at a concentration of nearly 80 $\mu$g/ml had no detectable effect on the response. These results demonstrate that antibody 4A5 interferes with the activity of VEGF-D mediated by VEGFR-2. The mouse hybridoma cells, 4A5$_A$, that produce antibody 4A5 have been deposited in the American Type Culture Collection, Manassas, Va. 20110-2209 USA on Apr. 16, 1999 (ATCC # HB-12698). The deposit was made under the requirements of the Budapest Treaty on the International Recognition of the Deposit of Microorganisms for the Purposes of Patent Procedure.

EXAMPLE V

Testing Antibodies for the Capacity to Interfere With the Binding of VEGF-D to Immobilized VEGFR-2 and VEFGR-3

Figure 3A:
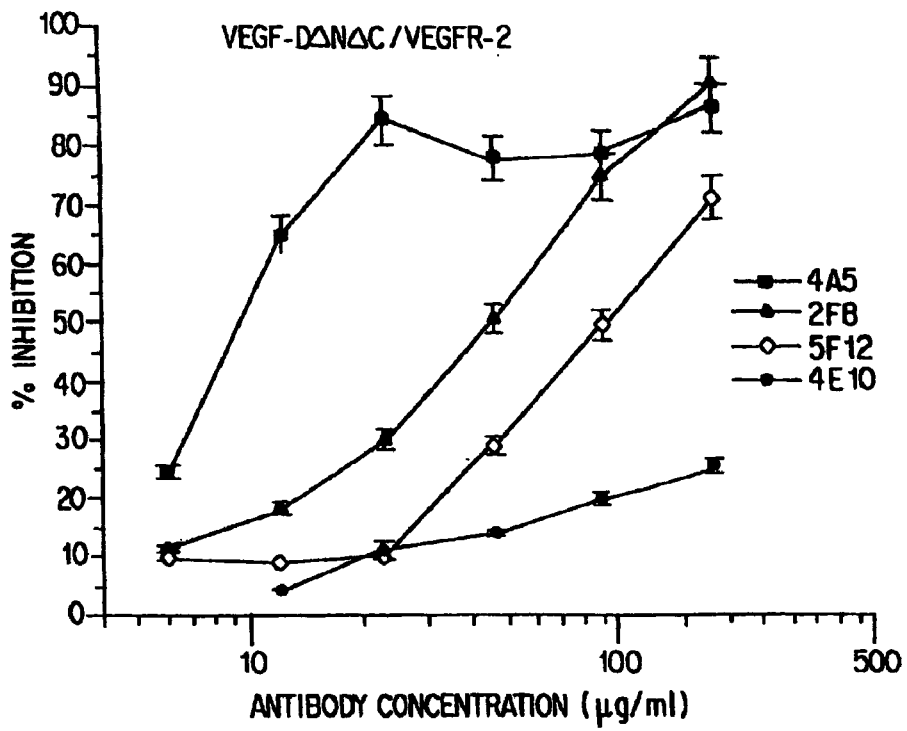
FIGS. 3A and 3B shows the relative binding affinities of the monoclonal antibodies for VEGF-DΔNΔC.
Figure 3B:
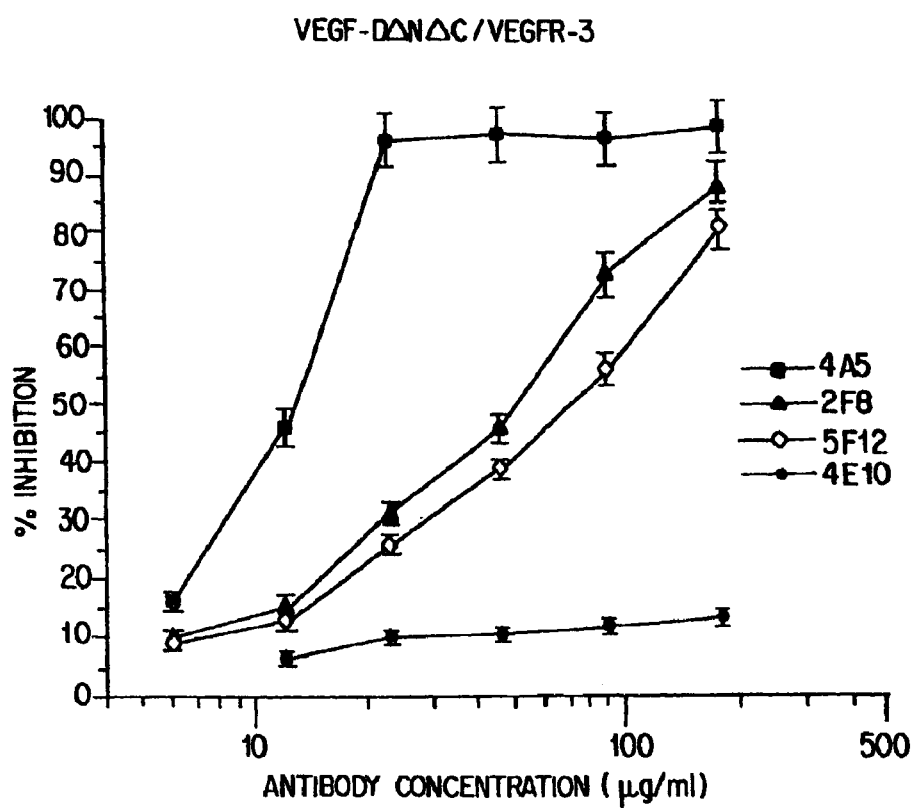

The inhibitory effect of antibody 4A5 in the bioassay in Example IV could be the effect of the antibody blocking the binding of VEGF-DΔNΔC to receptor or subsequent receptor cross-linking. The bioassay of Example IV cannot distinguish between inhibition by these two distinct mechanisms. In order to directly study the effect of the four anti-VEGF-DΔNΔC MAbs, 2F8, 4A5, 4E10 and 5F12, on the binding of VEGF-DΔNΔC to the respective receptors, the interaction of VEGF-DΔNΔC with immobilized receptor extracellular domains were analyzed with a biosensor. The extracellular domain of mouse VEGFR-2 (VEGFR-2-FLAG) and a chimeric protein consisting of the extracellular domain of human VEGFR-3 and the Fc portion of human IgG$_1$ (VEGFR-3-Ig) were immobilized onto sensor chips as described in Example III (4677 and 5113 RU immobilized equivalent to 4.7 and 5.1 ng/mm$^2$ respectively). The effects of the antibodies on receptor interactions were determined by flowing mixtures of purified human VEGF-DΔNΔC (61 nM), preincubated with varying concentrations (37.5 to 1200 nM) of the antibodies for VEGF-DΔNΔC for 1 hour in PBS at 4° C. 30 μl aliquots of the mixtures containing human VEGF-DΔNΔC at 2 μg/ml and varying-concentrations of antibodies as shown in FIGS. 3A and 3B were injected over the sensor chips at a flow rate of 10 μl/ml. FIGS. 3A and 3B show that results of this assay. Antibody 4A5 was sufficient to almost totally block binding to both receptors. Antibodies 2F8 and 5F12 also inhibited interactions with both receptors but at a much higher antibody concentrations than 4A5. An approximately forty-fold molar excess of 2F8 and 5F12 was required to almost block binding to both receptors. In contrast, 4E10 had only marginal effects. These data indicated that antibodies 4A5, 2F8 and 5F12 will be useful for analyses of the biological function of VEGF-D and for inhibition of VEGF-D bioactivity in a clinical context. The percentage inhibition of binding was calculated using the biosensor signals observed at the beginning of dissociation phase in the presence of competitor (RUc) and the signal observed with VEGF-DΔNΔC injected at 2 μg/ml in the presence of a non-specific control antibody (anti-EGFR MAb 528 (8)) (RUt) as follows: %Competition=RUt-RUc/RUt×100.

EXAMPLE VI

Testing Antibodies for the Capacity to Interfere With the Activity of VEGF Mediated By VEGFR-2

Figure 4:
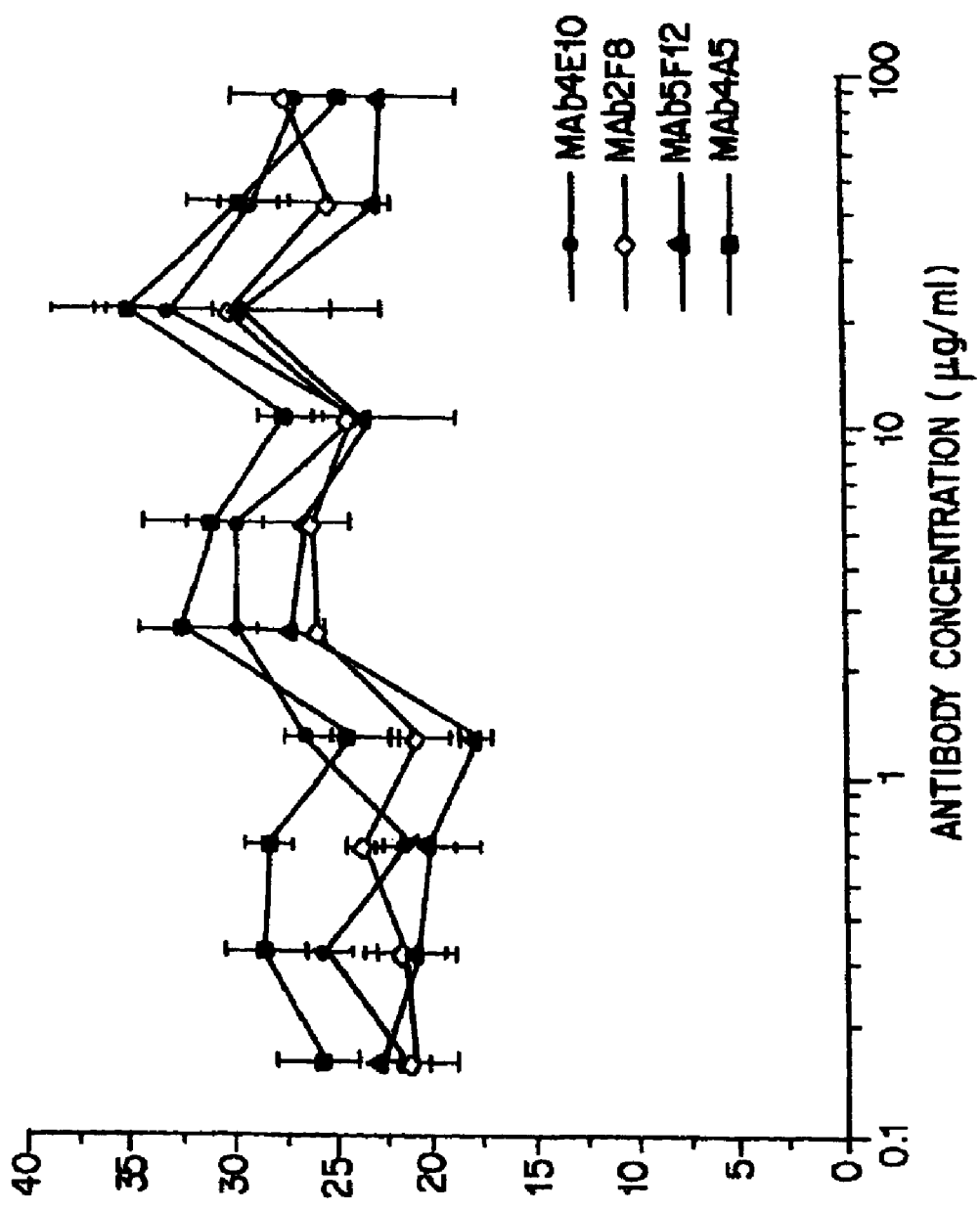
FIG. 4 shows the effects of the monoclonal antibodies on the response of Ba/F3-NYK-EpoR cells to murine VEGF$_{164}$.
Figure 5:
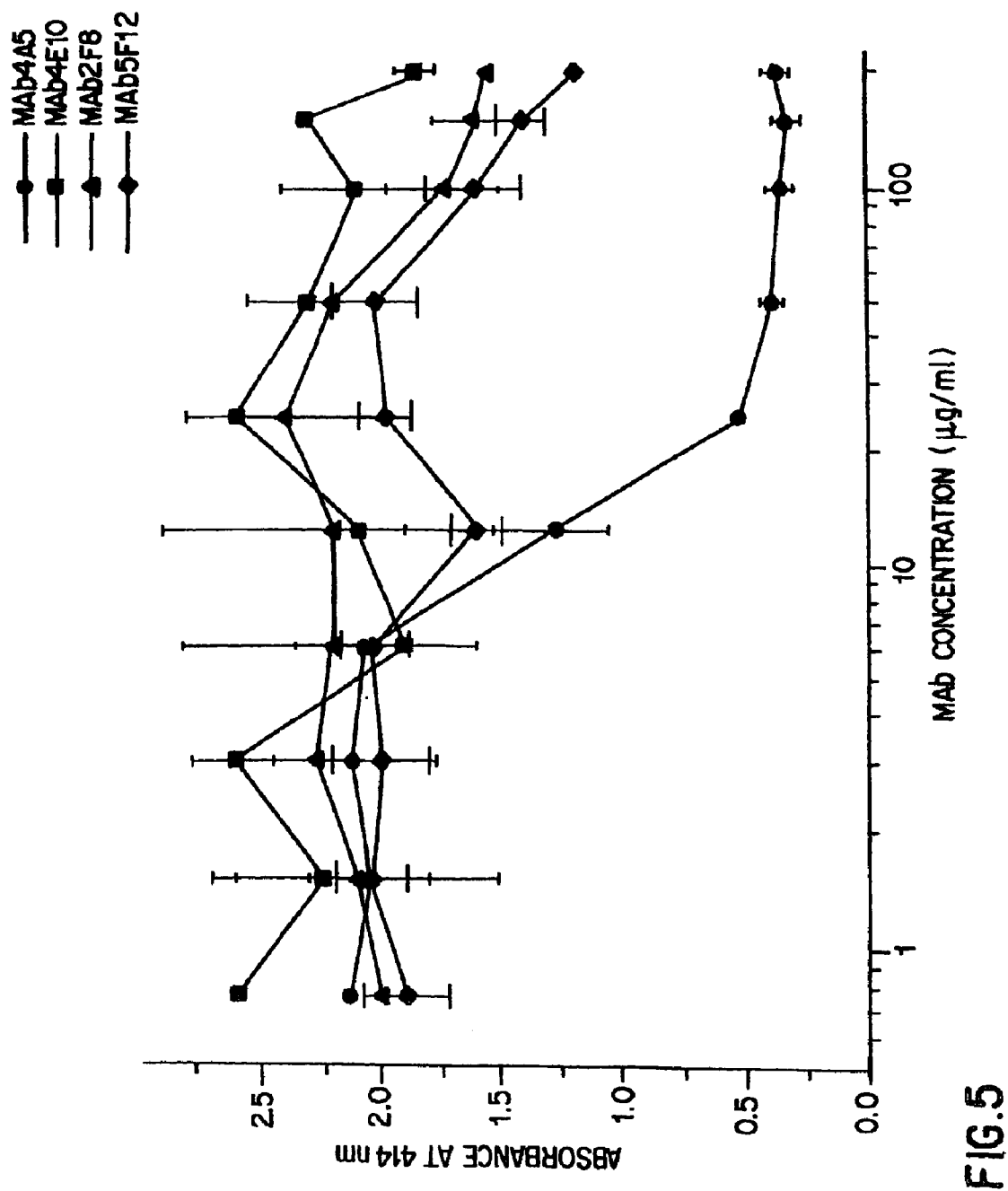
FIG. 5 shows the effects of anti-VEGF-D MAbs on the binding of VEGF-DΔNΔC to the extracellular domain of VEGFR-3.

As a control, antibodies were tested for their capacity to interfere with the proliferative response of Ba/F3-NYK-EpoR cells to purified murine VEGF$_{164}$. The results of these tests are shown in FIG. 4. None of the antibodies had any significant effect on the response of the cells to murine VEGF$_{164}$. These results demonstrate that antibody 4A5 interferes with the activity of VEGF-D mediated by VEGFR-2, but does not interfere with the activity of VEGF mediated by this receptor.

EXAMPLE VII

Testing Antibodies for the Capacity to Bind to VEGF-C

The same enzyme immunoassay as described above was used to test the four VEGF-D MAbs for the capacity to bind to VEGF-CΔNΔC. VEGF-CΔNΔC consists of the VEGF homology domain (VHD) of VEGF-C (residues 103 to 215) and is the region of VEGF-C which is most identical to VEGF-DΔNΔC. VEGF-CΔNΔC, to which a 6×histidine tag had been added at the C-terminus, was expressed in strain GS115 of the yeast *P. pastoris* using the expression vector pIC9 (Invitrogen, San Diego, Calif.) according to manufacturer's instructions and purified using Ni-NTA Superflow resin (QIAGEN, Valencia, Calif.). Of the four antibodies tested by this immunoassay, only 4E10 bound to VEGF-CΔNΔC.

EXAMPLE VIII

Antibodies which Interfere With the Binding of VEGF-D to VEGFR-3

The four anti-VEGF-DΔNΔC MAbs, 2F8, 4A5, 4E10 and 5F12, were tested for the capacity to interfere with the binding of VEGF-DΔNΔC to the extracellular domain of VEGFR-3 using an in vitro receptor-binding assay. A plasmid construct encoding a chimeric protein consisting of the extracellular domain of human VEGFR-3 and the Fc portion of human IgG (K. Pajusola, Biotechnology Institute, Helsinki) was transfected into 293-EBNA cells using Fugene 6 (Boehringer Mannheim, Germany) according to the instructions provided by the manufacturer. The chimeric protein was purified from cell supernatants by gentle agitation with Protein A Sepharose beads (Amersham, UK) overnight at 4° C. and elution with 100 mM glycine-HCl, pH 2.8. The presence of the chimeric protein in the eluate was confirmed by using a small proportion of the sample for Western blot analysis with peroxidase-conjugated affinity purified goat anti-human IgG, Fc fragment-specific antibody (Jackson Immunoresearch Labs., West Grove, Pa.). The remainder of the sample was diluted 1:3 with 50 mM sodium bicarbonate buffer (pH 9.6), concentrated approximately 4-fold using a Centricon 10 concentrator (Amicon, Beverly, Mass.) and incubated at 37° C. for one hour in the wells of a 96-well microtiter plate (Linbro/Titertek, ICN Biomedicals, Aurora, Ohio). After removal of the solution containing the chimeric protein, plates were washed extensively with PBS and 0.05% Tween 20 (PT20) and blocked with 1% bovine serum albumin in PBS for 30 minutes at room temperature. The plates were washed again with PT20 and then incubated with PBS containing VEGF-DΔNΔC (7.3 μg/ml) and MAbs for one hour at room temperature. Before addition to the microtiter plate, the VEGF-DΔNC and MAbs had been incubated together for one hour at 4° C. After incubation with the solution of VEGF-DΔNΔC and MAbs, the plates were washed with PT20 and incubated by shaking with PBS containing 3.5 μg/ml of biotinylated M2 anti-FLAG MAb (Sigma, St. Louis, Mo.) for two hours at 4° C. The M2 MAb could be used to detect VEGF-DΔNΔC bound to VEGFR-3 in the receptor-binding assay because the polypeptide is tagged at the N-terminus with the FLAG® octapeptide (Sigma, St. Louis, Mo.). The plates were next washed with PT20, incubated with streptavidin-peroxidase conjugate (Boehringer Mannheim, Germany) shaking for one hour at 4° C. and washed again with PT20. The assay was then developed with the ABTS substrate system (Zymed, San Francisco, Calif.) and quantitated by reading absorbance at 414 nm in a multiwell plate reader (Flow Laboratories MCC/340, McLean, Va.).

Two negative controls were developed for the assay. First, 293-EBNA cells were transfected with a plasmid construct expressing a chimeric protein consisting of the extracellular domain of human VEGFR-1 and the Fc portion of human IgG (E. Korpelainen, Haartman Institute, Helsinki). Transfection of the 293-EBNA cells, purification of the chimeric protein, analysis by Western blot and the binding assay (in the absence of MAbs) were carried out exactly as described above. The VEGFR-1/Ig protein acts as a negative control for the assay because VEGF-DΔNΔC does not bind to VEGFR-1. Second, 293-EBNA cells were transfected with an expression vector lacking sequences encoding VEGF receptors. Conditioned medium from these cells was used exactly as those containing VEGFR-3/Ig and VEGFR-1/Ig chimeric proteins.

In order to test if the four MAbs interfered with the binding of the M2 MAb to VEGF-DΔNΔC, affinity-purified VEGF-DΔNΔC was coated onto the surface of microtiter plates by incubation at 37° C. for one hour in 50 mM sodium bicarbonate id buffer (pH 9.6). The plates were then washed with PT20, incubated in the presence or absence of anti-VEGF-D MAbs for one hour at 4° C., washed again with PT20 and incubated with biotinylated M2 MAb, washed, developed and quantitated as described above. These control assays were carried out with a constant amount of VEGF-DΔNΔC and the same range of concentrations of the four anti-VEGF-D MAbs used in the receptor-binding assay. In addition, controls were carried out with a constant concentration of each MAb (200 µg/ml) and approximately a 100-fold range of VEGF-DΔNΔC concentrations. In both sets of controls, detection of VEGF-DΔNΔC by biotinylated M2 MAb was identical in the presence or absence of anti-VEGF-D MAbs, irrespective of the concentrations of anti-VEGF-D MAbs or of VEGF-DΔNΔC in the assays. These control assays demonstrated that none of the four MAbs tested had any effect whatsoever on the binding of the M2 MAb to VEGF-DΔNΔC.

The effect of the four VEGF-D MAbs on the binding of VEGF-DΔNΔC to VEGFR-3 is shown in FIG. 4. The MAb concentration denotes the concentration of each MAb in the solution with VEGF-DΔNΔC in the wells of the microtiter plates. Each curve represents the results of two assays and the error bars denote the range of absorbance measured in the two experiments at each antibody concentration. MAb 4E10 had no effect on this interaction even up to a concentration of 200 µg/ml. In contrast, MAb 4A5 at a concentration of 25 µg/ml was sufficient to almost totally block the interaction between the ligand and the extracellular domain of VEGFR-3. MAbs 2F8 and 5F12 had minor inhibitory effects at concentrations above 90 μg/ml, that were far less striking than the effect of 4A5. Negative controls, lacking anti-VEGF-D MAbs, generated from cells expressing either a VEGFR-1/Ig chimeric protein or no VEGF receptor derivatives both gave an absorbance which was equal to that of the VEGFR-3/Ig assays when MAb 4A5 was included at a concentration of 200 μg/ml, i.e. when the interaction of VEGF-DΔNΔC with VEGFR-3 had been totally blocked. This demonstrated that the binding of VEGF-DΔNΔC to the microtiter plates in the assays was dependent on the extracellular domain of VEGFR-3.

Where the antibody is to be used for therapeutic purposes, the dose and route of application will depend upon the nature of the patient and condition to be treated, and will be at the discretion of the attending physician or veterinarian. Suitable routes include subcutaneous, intramuscular, intraperitoneal or intravenous injection, topical application, implants etc. Topical application of the antibody may be used in a manner analogous to VEGF.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A method of detecting VEGF-D in biological sample, comprising the step of contacting the sample with an antibody or an antibody labeled with a detectable label which specifically binds to a polypeptide comprising an amino acid sequence of SEQ ID NO:1, wherein said antibody is selected from the group consisting of a monoclonal antibody of 2F8 (ATCC No. PTA-3653), 4A5 (ATCC No. HB-12698), 4E10 (ATCC No. PTA-3652, and 5F12 (ATCC No. PTA-3651), or a F(ab')$_2$, F(ab'), or F(ab) fragment thereof, or a chimeric antibody thereof or a humanized antibody thereof, and detecting the occurrence of binding of said antibody to VEGF-D.

2. A method of detecting VEGF-D in biological sample, comprising the step of contacting the sample with an antibody or an antibody labeled with a detectable label which interferes with an activity of VEGF-D mediated by a VEGF receptor-2 or VEGF receptor-3, wherein said antibody is selected from the group consisting of a monoclonal antibody of 2F8 (ATCC No. PTA-3653), 4A5 (ATCC No. HB-12698), 4E10 (ATCC No. PTA-3652, and 5F12 (ATCC No. PTA-3651), or a F(ab')$_2$, F(ab'), or F(ab) fragment thereof, or a chimeric antibody thereof or a humanized antibody thereof, and detecting the occurrence of binding of said antibody to VEGF-D.

3. The method according to claim 1, wherein said antibody or said antibody labeled with a detectable label is a monoclonal antibody or a F(ab')$_2$, F(ab'), or F(ab) fragment thereof, or a chimeric antibody thereof.

4. The method according to claim 3, wherein said antibody is labeled with a detectable label.

5. The method according to claim 4, wherein said detectable label is a radioactive isotope.

6. The method according to claim 1, wherein said antibody is a humanized antibody.

7. The method according to claim 1, wherein said antibody is selected from the group consisting of 2F8 (ATCC No. PTA-3653), 4A5 (ATCC No. HB-12698), 4E10 (ATCC No. PTA-3652), and 5F12 (ATCC No. PTA-3651), or a F(ab')$_2$, F(ab'), or F(ab) fragment thereof.

8. The method according to claim 1, wherein said antibody is Mab 4A5 (ATCC No. HB-12698) or a F(ab')$_2$, F(ab'), or F(ab) fragment thereof.

9. The method according to claim 1, wherein said antibody interferes with an activity of VEGF-D mediated by a VEGF receptor-2, and is a monoclonal antibody, or a F(ab')$_2$, F(ab'), or F(ab) fragment or a chimeric antibody thereof.

10. The method according to claim 1, wherein said antibody interferes with the binding of VEGF-D to a VEGF receptor-3.

11. The method according to claim 1, wherein said antibody interferes with the binding of VEGF-D to a VEGF receptor-3, and is a monoclonal antibody, or a F(ab')$_2$, F(ab'), or F(ab) fragment thereof or a chimeric antibody thereof.

12. The method according to claim 2, wherein said antibody specifically binds to a polypeptide comprising the amino acid sequence of SEQ ID NO:1.

13. The method according to claim 2, wherein said antibody is a monoclonal antibody, or a F(ab')$_2$, F(ab'), or F(ab) fragment or a chimeric antibody thereof.

14. The method according to claim 2, wherein said antibody is labeled with a detectable label.

15. The method according to claim 14, wherein said detectable label is a radioactive isotope.

16. The method according to claim 2, wherein said antibody is a humanized antibody.

17. The method according to claim 2, wherein said antibody is selected from the group consisting of 2F8 (ATCC No. PTA-3653), 4A5 (ATCC No. HB-12698), 4E10 (ATCC No. PTA-3652), and 5F12 (ATCC No. PTA-3651), or a F(ab')$_2$, F(ab'), or F(ab) fragment thereof.

18. The method according to claim 2, wherein said antibody is Mab 4A5 (ATCC No. HB-12698) or a F(ab')$_2$, F(ab'), or F(ab) fragment thereof.

19. The method according to claim 2, wherein said antibody interferes with the binding of VEGF-D to a VEGF receptor-3.

20. The method according to claim 2, wherein said antibody interferes with the binding of VEGF-D mediated by a VEGF receptor-3, and is a monoclonal antibody, or a F(ab')$_2$, F(ab'), or F(ab) fragment or a chimeric antibody thereof.

* * * * *

```
                         SEQUENCE LISTING

<160> NUMBER OF SEQ ID NOS: 1

<210> SEQ ID NO 1
<211> LENGTH: 109
<212> TYPE: PRT
<213> ORGANISM: Homo sapiens

<400> SEQUENCE: 1

Phe Tyr Asp Ile Glu Thr Leu Lys Val Ile Asp Glu Glu Trp Gln Arg
  1               5                  10                  15

Thr Gln Cys Ser Pro Arg Glu Thr Cys Val Glu Val Ala Ser Glu Leu
             20                  25                  30

Gly Lys Ser Thr Asn Thr Phe Phe Lys Pro Pro Cys Val Asn Val Phe
         35                  40                  45

Arg Cys Gly Gly Cys Cys Asn Glu Glu Ser Leu Ile Cys Met Asn Thr
     50                  55                  60

Ser Thr Ser Tyr Ile Ser Lys Gln Leu Phe Glu Ile Ser Val Pro Leu
 65                  70                  75                  80
```

```
                            -continued

Thr Ser Val Pro Glu Leu Val Pro Val Lys Val Ala Asn His Thr Gly
                85                  90                  95

Cys Lys Cys Leu Pro Thr Ala Pro Arg His Pro Tyr Ser
            100                 105
```